Sept. 1, 1953 W. E. LAMMERTS Plant Pat. 1,215
CAMELLIA PLANT
Filed Oct. 8, 1952 2 Sheets-Sheet 1
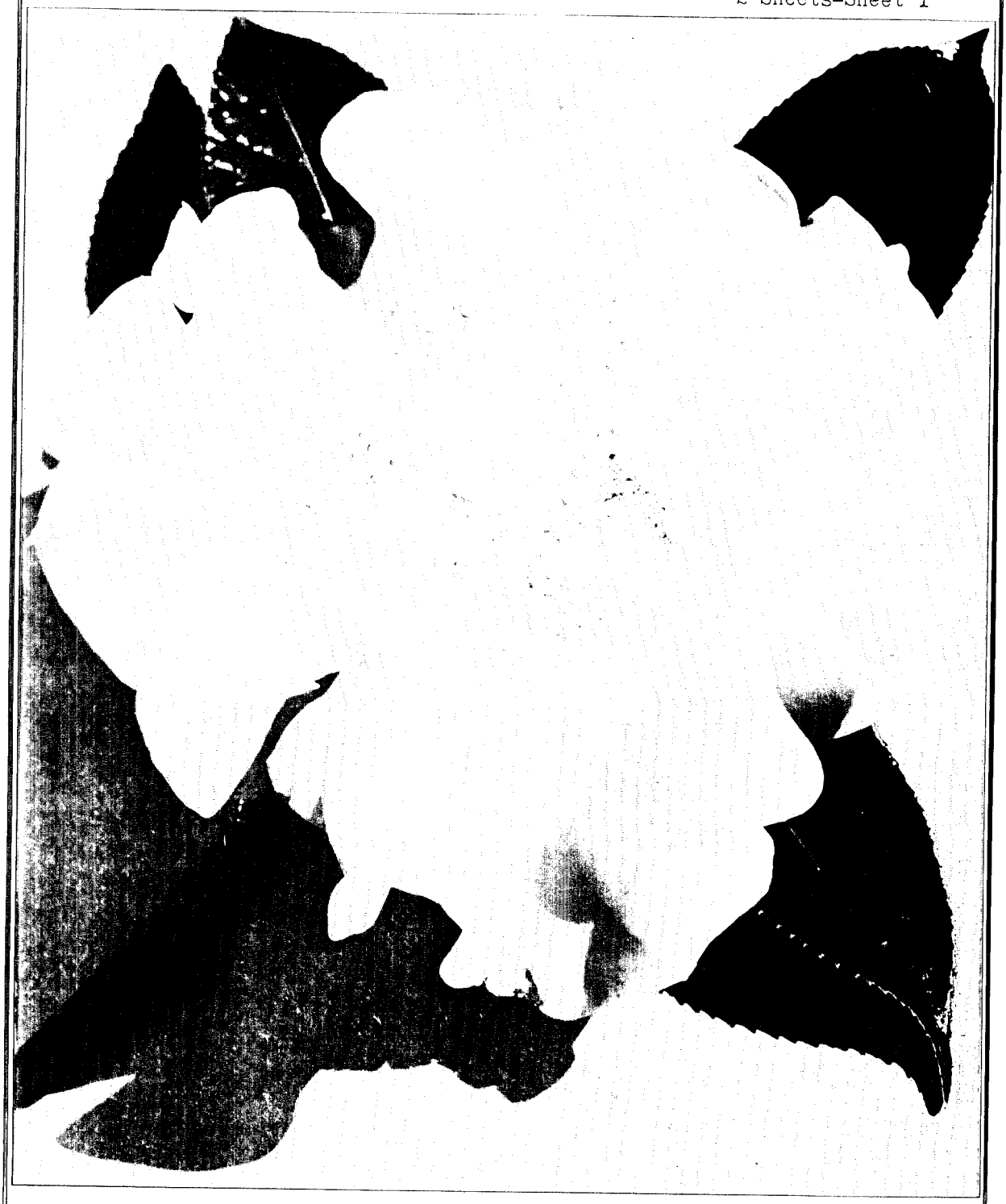
Inventor.
W. E. Lammerts
By: Robert Sept. 1, 1953 W. E. LAMMERTS Plant Pat. 1,215
CAMELLIA PLANT
Filed Oct. 8, 1952 2 Sheets-Sheet 2
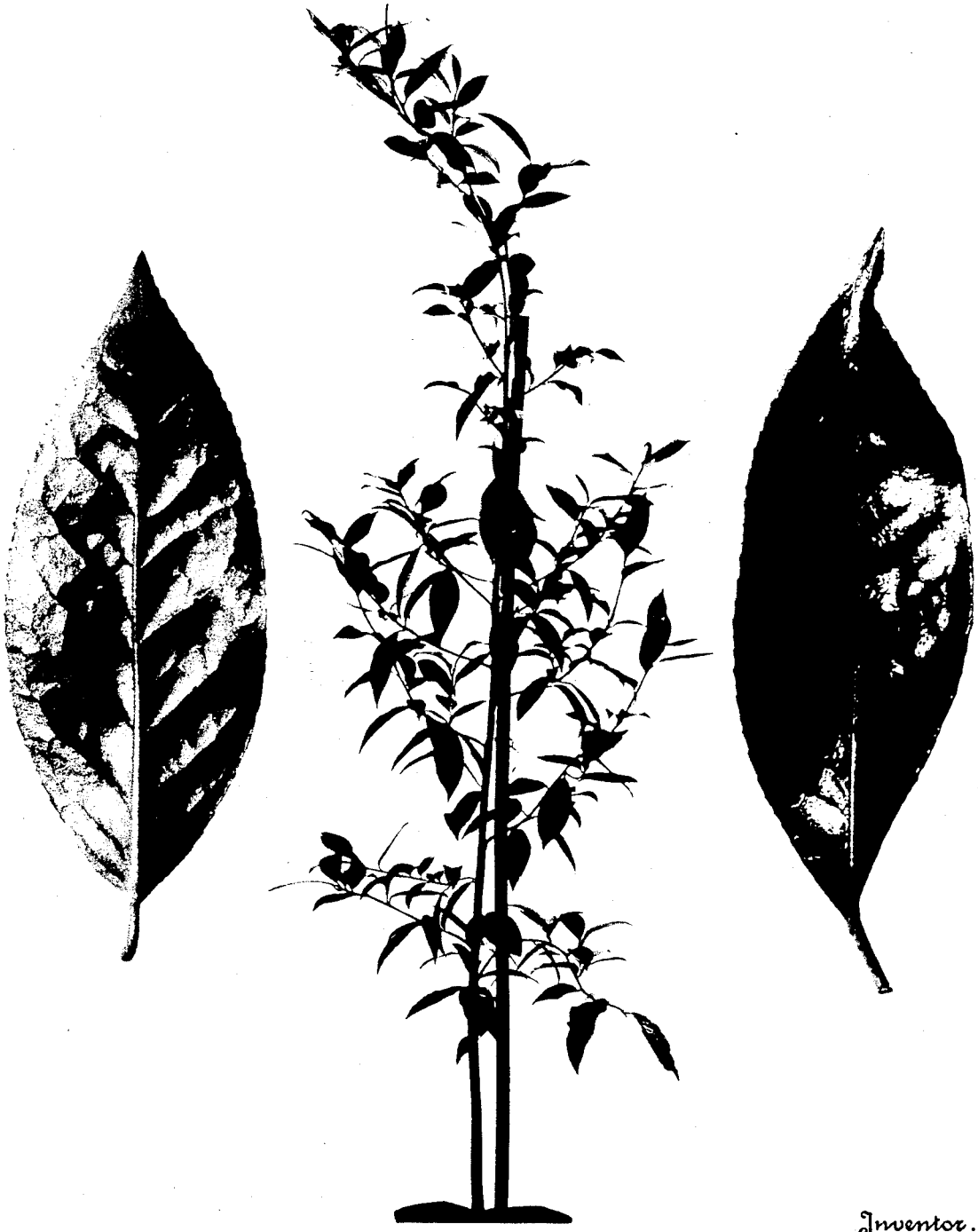
Inventor.
W. E. Lammerts
By Robbs & Cobb
Attorneys.

Patented Sept. 1, 1953

Plant Pat. 1,215

UNITED STATES PATENT OFFICE 1,215

CAMELLIA PLANT

Walter E. Lammerts, La Canada, Calif., assignor to Descanso Distributors, Inc., La Canada, Calif., a corporation of California Application October 8, 1952, Serial No. 313,818

1 Claim. (Cl. 47—69)

The present invention relates to a new and distinct variety of camellia plant originated by crossing the *C. reticulata* variety "Early Peach Bloom" (unpatented) with an unnamed and unpatented variation of the variety *C. pitardii.*

As the result of this cross, a new variety of camellia has been produced, said new variety being substantially different from either parent, as well as from all other varieties of its class, as evidenced by the following combination of unique, dominant characteristics:

(1) Unlike the *C. japonica* varieties, this new camellia undergoes unusual transformations in form, the petals gradually increasing in size and becoming more arched inward and arcuate in shape as the flower ages, thereby giving the flower an unusually great depth from the outer end to the base thereof;

(2) At maturity, the flowers are exceptionally large and average from 4¾ inches to 6½ inches in diameter;

(3) The flowers have an unusal open-flower form, and the inner petals thereof arch upwardly and inwardly so as to present an arcuate shape;

(4) The unusually great depth of the open-flowers, averaging from 2½ inches to 3 inches; and (5) The flowers have an unusual and uniform Phlox Pink color in general color tonality, with veins of Tyrian Rose.

Asexual reproduction of the new variety by graftings at La Canada, California, shows that the foregoing characteristics and distinctions come true to form and are established and transmitted through succeeding propagations.

The accompanying drawings show a typical specimen plant, flower and leaves of the new variety, with the flower specimen illustrated in color.

The following is a detailed description of the new variety, based upon observations as made at La Canada, California, with color terminology in accordance with Robert F. Wilson Horticultural Colour Chart, except where general color terms of ordinary dictionary significance are obvious:

Breeding: Seedling.

*Seed parent.*—*C. reticulata* variety "Early Peach Bloom."

*Pollen parent.*—An unnamed variation of the variety *C. pitardii.*

Propagation: Holds its distinguishing characteristics through succeeding propagations by grafting.

Blooming habit: Blooms about mid-season, usually in February and March in southern California.

Bud:

*Size.*—Large; about 2 inches long from base of calyx and 1¼ inches wide at tips of calyx lobes.

*Form.*—Long; urn to ovoid in shape.

*Color.*—Rose Red, Plate 724; opening bud Tyrian Rose, Plate 24.

*Sepals.*—Smooth edged, but ciliate margined with silvery hairs up to $\frac{1}{32}$ inch long.

*Calyx.*—Consists of 6 sepals which are imbricate, the two inner being much longer than the others (about 1 inch long), tinged Tyrian Rose, Plate 24/1 on sides towards base; outer surface of sepals silvery-haired; several bract-like sepals at base of calyx. Shape—cup-shaped. Size—large; broad.

Bloom:

*Size (when fully open).*—Large; 4¾ inches to 6½ inches.

*Borne.*—Singly, on normal strength, medium length stems.

*Form.*—When first petal opens—cupped. When fully open—flat, with inner petals arched upward and inward; arcuate shape.

*Petalage.*—Semi-double; arranged regularly; 10 to 12 petals.

*Color.*—Varying from Crimson, Plate 22/1 as flower first opens, to Phlox Pink, Plate 625, and finally to Plate 625/2 as flower ages: with veins of Tyrian Rose, Plate 24/2.

Petals: Thick; soft; with inside and outside satiny.

*Shape.*—Oval; waved and crinkled on margins from center to base of petal.

*Arrangement.*—Informal; imbricated.

*Lasting quality.*—On plant, 5 to 6 days. As cut flower, 3 to 4 days.

*Genital organs*

Stamens, anthers: Medium size; many.

*Color.*—Golden yellow.

*Arrangement.*—In circle around central styles.

Stamens, filaments: Medium length. Color—straw yellow.

Pollen: Color—Aureolin, Plate 3/1.

Styles: Loosely separated; uneven length; long. Color—straw yellow.

Ovaries: All enclosed in calyx.

Fruit: None.

Form of plant: Very tall, slender shrub; loosely branched; lower branches often drooping.

Growth: Very vigorous; upright; of open rangy habit.

Foliage:

*Size.*—Large; 4½ inches to 5½ inches long; 1½ inches to 2¼ inches wide.

*Quality.*—Abundant.

*Color.*—New foliage: upper surface—near Scheele's Green, Plate 860; lower surface—near Lettuce Green, Plate 861. Old foliage: upper surface — near Spinach Green, Plate 0960; lower surface—near Spinach Green, Plate 0960/2.

*Shape.*—Lanceolate; terminating in long point at end, averaging ¼ inch to ⅜ inch wide at base by ⅝ inch to ¾ inch long.

*Texture.*—Upper side—glossy; reticulate due to both primary and secondary veins being indented; completely glabrous. Under side—glossy; glabrous.

*Ribs and veins.*—Prominent on under side.

*Edge.*—Finely serrate.

Wood:

*New wood.*—Color—near Fern Green, Plate 0862/3, tinged heavily with brown on sides of stem facing light source.

*Old wood.*—Color—greyish-brown.

I claim:

A new and distinct variety of camellia plant, substantially as herein shown and described, characterized particularly as to novelty by its unusually large flowers of open-flower form, by the arcuate shape of its flowers resulting from the upwardly and inwardly arched form of the petals thereof, by the substantial uniformity of the Phlox Pink general color tonality of its flowers, with veins of Tyrian Rose, and by the unusual transformations in the form of the flowers, the petals of which gradually increase in size and become more arched inward and more arcuate in shape as the flowers age, thereby giving the mature flowers an unusually great depth.

WALTER E. LAMMERTS.

No references cited.